United States Patent [19]

O'Lenick, Jr.

[11] Patent Number: 5,235,017

[45] Date of Patent: Aug. 10, 1993

[54] FLUORINE CONTAINING SILICONE POLYESTER COMPOUNDS

[75] Inventor: Anthony J. O'Lenick, Jr., Lilburn, Ga.

[73] Assignee: Siltech Corporation, Toronto, Canada

[21] Appl. No.: 935,420

[22] Filed: Aug. 26, 1992

Related U.S. Application Data

[63] Continuation-in-part of Ser. No. 837,152, Feb. 19, 1992, Pat. No. 5,164,471.

[51] Int. Cl.$^5$ .............................................. C08G 77/06
[52] U.S. Cl. ........................................ 528/26; 528/42; 528/29; 525/446; 525/474
[58] Field of Search ..................... 528/26, 42, 29; 525/474, 446

[56] References Cited

U.S. PATENT DOCUMENTS

| | | | |
|---|---|---|---|
| 3,038,000 | 6/1962 | Schmidt | 528/42 |
| 4,937,277 | 6/1990 | O'Lenick, Jr. | 524/318 |
| 5,051,489 | 9/1991 | O'Lenick, Jr. | 528/26 |
| 5,126,420 | 6/1992 | Satoh et al. | 528/32 |
| 5,164,471 | 11/1992 | O'Lenick, Jr. | 528/26 |

Primary Examiner—John C. Bleutge
Assistant Examiner—Margaret W. Glass

[57] ABSTRACT

The invention discloses novel fluorine containing polyester compounds. Compounds of the invention by virtue of (a) the silicone containing polyester group, (b) the fluorine containing terminal groups and (c) the polyoxyalkylene containing dimethicone copolyol group are extremely efficient lubricating materials when applied to a variety of surfaces and are water dispersible or water soluble depending upon the specific molecule. These materials have a water soluble portion in the silicone backbone which allows for the preparation of water dispersible and water soluble fluorine containing compounds useful in personal care applications as conditioners and softeners. The compounds of the present invention are prepared by reacting a dimethicone copolyol compound with a dicarboxylic acid and a fluorine containing alcohol.

15 Claims, No Drawings

FLUORINE CONTAINING SILICONE POLYESTER COMPOUNDS

RELATED APPLICATION

This application is a continuation in part of copending U.S. application Ser. No. 837,152 filed Feb. 19, 1992, now U.S. Pat. No. 5,164,471.

BACKGROUND OF THE INVENTION

1. Field of the Invention

The present invention relates to a series of novel fluorine containing silicone polyesters which provide outstanding lubrication, conditioning and nonocclusive coatings to hair and skin. Unlike the compounds of the invention disclosed in the application of which this is a continuation in part, the compounds of the present invention are water dispersible or water soluble, allowing for them to provide conditioning and breathable films when applied from aqueous solution to hair and skin. The esterification by which the compounds are prepared is the reaction of a dimethicone copolyol, a hydroxy containing silicone polymer which may contain varying amounts of polyoxyalkylene in the molecule, a dicarboxylic acid and a fluorine containing alcohol. In the instance where the fluorine containing alcohol contains only one hydroxyl group, it will become a terminal group in the polyester.

ARTS AND PRACTICES

Silicone compounds have been known to be active at the surface of plastic, cellulosic and synthetic fibers as well as paper. They are good nondurable lubricants and are very stable to oxidation, however, their high cost and lack of efficiency at low concentrations as well as low durability have made their acceptance in commercial products quite low. In all instances, commercially available quaternaries are the active ingredient in traditional laundry care markets, with little or no silicone added.

The low efficiency and low durability of dimethylpolysiloxane is due to the fact that it is very water insoluble and deposits on the surface to obtain a minimum free energy in the solution. Simply, the silicone oil delivery to the surface by hydrophobic binding, not chemical bonding. At the surface, the dimethylpolysiloxane is a very effective fiber lubricant, however, there are two drawbacks, first; the dimethylpolysiloxane is not chemically bonded so the effect is very transient and disappears with one washing, and second; since there is no reaction of the dimethylpolysiloxane to the surface an equilibrium between fiber absorbed dimethylpolysiloxane and dimethylpolysiloxane in the dispersion results in very inefficient percentage of silicone deposited. A large amount of the expensive silicone goes down the drain with the waste water.

In many applications, there is a strong desire to obtain a solid wax which can be used in applications were a spread on application is of interest. These applications include personal care applications like antiperspirants and skin creams. Unfortunately most silicone derivatives are liquid to very low temperatures. Attempts to overcome this deficiency have been made by reacting stearyl alcohol with a chloro silane. The difficulty with the use of this type of material is that a large excess (50% by weight) of the alcohol needs to be added to get a product which is free of the irritating chlorosilane raw material. When such an excess is used the product behaves functionally more like the stearyl alcohol than like a silicone compound. Additionally, the compound is not polymeric, hence the superior lubrication and hydrophobicity enhancements which can be achieved by dimethylpolysiloxane is not obtainable with these compounds.

U.S. Pat. No. 3,511,699 to Sterman issued May 12, 1970 teaches that epoxy compounds placed in the silicone backbone by hydrosilation can be cured onto certain fibers to give improved substantivity. The substantivity is based upon the reaction of hydroxyl groups on the cellulosic and the epoxy group in the silicone polymer. The resulting bond is a ether linkage and a new hydroxyl group. While a definite improvement over other compounds the efficiency and durability of the were not good enough to allow for cost effective incorporation of these materials in detergent formulations.

U.S. Pat. No. 5,051,489 issued to O'Lenick, Jr. teaches that silicone esters can be prepared by the reaction of silanols and fatty acids. These compounds lack the critical fluorine containing component.

THE INVENTION

Object of the Invention

It is the object of the present invention to provide a water dispersible novel fluorine containing dimethicone copolyol based polyester compound which is spreads our into a very thin durable film and provides outstanding conditioning when applied to a variety of surfaces, most importantly skin and hair.

It is another objective of the current invention to provide fluorine containing polyesters which can be used in textile, and personal care applications to render softness and lubrication to the substrates being treated.

The incorporation of fluorine into the polyester results in the improved spreading and the ability to use these materials at heretofore unknown concentrations and still obtain efficacy. The use of dimethicone copolyols as raw material hydroxy containing silicone compounds allows for the preparation of water dispersible to water soluble polyesters which are substantive to hair and skin. It is not possible to make water dispersible or water soluble materials using the technology disclosed in the related patent application, which are based upon silanol compounds. This is because there is no practical method of introducing the desired polyoxyalkylene moiety into the compound.

SUMMARY OF THE INVENTION

The present invention relates to novel fluorine containing water dispersible or water soluble silicone polyester compounds. Compounds of the invention by virtue of (a) the polyester group, (b) the fluorine containing terminal groups and (c) the polyoxyalkylene portion of the molecule present in the dimethicone copolyol are extremely efficient lubricating materials when applied to a variety of surfaces and are water dispersible or water soluble. These materials spread out when applied and provide durable lubrication and hydrophobicity when applied to hair, skin, wood, plastic and textile fibers. The compounds of the present invention are prepared by reacting a dimethicone copolyol compound with a polycarboxylic acid and a fluorine containing alcohol.

The compounds of this invention are fluorine containing dimethicone copolyol polyesters made by the esterification of a dicarboxylic acid, ester or anhydride, a dimethicone copolyol compound and a fluorine containing alcohol. Specifically, the compounds of the present invention are fluorine containing polyester compounds which is prepared by the esterification reaction of;

(a) a dimethicone copolyol compound conforming to the following structure;

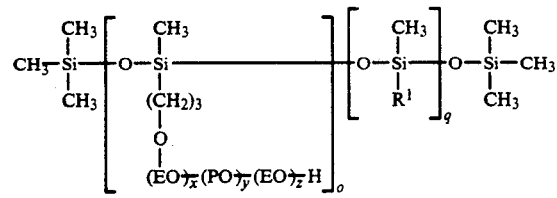

wherein;
R$^1$ is selected from the group consisting of CH$_3$ and phenyl;
EO is —(CH$_2$—CH$_2$—O—)—
PO is —(—CH$_2$—CH(CH$_3$)—O—)—
o is an integer ranging from 1 to 20;
q is an integer ranging from 0 to 200;
x, y and z are independently integers each ranging from 0 to 20;

(b) a diacid selected from the group consisting of HO(O)C—(CH$_2$)$_c$—C(O)OH, HO(O)C—(CH$_2$)$_d$—CH=CH—(CH$_2$)$_e$—C(O)OH and dimer acid; c, d and e are independently integers from 1 to 10; and (c) a fluorine containing hydroxy compound conforming to the following structure;

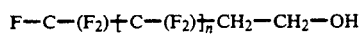

n is ranges from 3 to 17.

Dimer acid is well known to those skilled in the art and are prepared by the thermal condensation of unsaturated fatty acids catalyzed by a small amount of montmorillonite clay are described in numerous patents by C. G. Gobel (U.S. Pat. Nos. 2,482,761, 2,793,219, 2,793,220, 2,955,121, 3,076,003 and 3,100,784), incorporated herein by reference. Basically, dimer acid is the Diels Alder reaction of unsaturated mono fatty acids containing 18 carbon atoms, to produce a 36 carbon diacid. There are basically three structures which result. They are;

| UNSATURATED SPECIES | |
|---|---|
| STRUCTURE | DESIGNATION |
| CH$_3$—(CH$_2$)$_g$—CH—(CH$_2$)$_f$—C(O)—OH<br>                                      |<br>CH$_3$—(CH$_2$)$_f$—CH=C—(CH$_2$)$_f$—C(O)—OH | Acyclic |
| (cyclic structure with CH$_2$)$_g$—C(O)OH, H—C—(CH$_2$)$_g$—COOH, H—C—CH=CH—(CH$_2$)$_r$—CH$_3$, (CH$_2$)$_r$—CH$_3$) | Monocyclic |
| | Bicyclic |

| UNSATURATED SPECIES | |
|---|---|
| STRUCTURE | DESIGNATION |
| (bicyclic structure with (CH$_2$)$_r$—C(O)OH, H—C—(CH$_2$)$_r$—C(O)—OH, CH$_3$—(CH$_2$)$_r$—C—H, (CH$_2$)$_r$—CH$_3$) | |

The compounds are then hydrogenated to remove the double bonds to give the following;

| HYDROGENATED SPECIES | |
|---|---|
| STRUCTURE | DESIGNATION |
| CH$_3$—(CH$_2$)$_g$—CH—(CH$_2$)$_f$—C(O)—OH<br>                                      |<br>CH$_3$—(CH$_2$)$_f$—CH$_2$CH—(CH$_2$)$_f$—C(O)—OH | Acyclic |
| (monocyclic hydrogenated structure) | Monocyclic |
| (bicyclic hydrogenated structure) | Bicyclic |

The above structures both in the hydrogenated and unsaturated forms are collectively referred to as "dimer acid" and the derivatives are referred to as those derived from a dimer acid residue.

PREFERRED EMBODIMENTS

In a preferred embodiment the fluorine content in the polymer ranges from 5% to 30% by weight.

In another preferred embodiment the fluorine content in the polymer ranges from 10% to 25% by weight.

In a preferred embodiment the diacid is dimer acid. This results in a material with superior conditioning effects on hair and skin and better compatibility in many organic oils.

In another preferred embodiment the diacid is dodecanedioic acid.

In a still another embodiment, the dimethicone copolyol has present polyoxyalkylene glycol units. That is the sum of x+y+z is greater than 0.

In a more preferred embodiment, the dimethicone copolyol has present several polyoxyalkylene glycol units. That is the sum of x+y+z is greater than 2.

In a more preferred embodiment, the dimethicone copolyol has present several polyoxyalkylene glycol units. That is the sum of x+y+z is greater than 5.

EXAMPLES

The compounds of the present invention are prepared by the reaction of a dimethicone copolyol compound a diacid and a fluorine containing alcohol. Examples of suitable reactants are as follows:

| | Reactants | |
|---|---|---|
| Diacids | Formula | Molecular Weight |
| Adipic Acid | HO(O)C(CH2)4C(O)OH | 130 |
| Succinic Acid | HO(O)C(CH2)2C(O)OH | 102 |
| Dodecanedioic Acid | HO(O)C(CH2)10C(O)OH | 230 |
| Dimer Acid | See Above | 286 |
| Maleic Acid | HO(O)C—CH=CH—C(O)OH | 100 |

Dimethicone Copolyol Compounds

Dimethicone Copolyol compounds are well known and are marketed in the trade under many names. The compounds conform to the following generic structure;

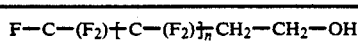

| Name | x | y | z | o | q |
|---|---|---|---|---|---|
| Siltech H 1000 | 3 | 0 | 0 | 2 | 54 |
| Siltech H 1100 | 10 | 5 | 10 | 10 | 100 |
| Siltech H 1200 | 20 | 20 | 20 | 2 | 56 |
| Siltech H 1300 | 10 | 10 | 10 | 6 | 26 |
| Siltech H 1400 | 0 | 10 | 0 | 4 | 200 |
| Siltech H 1500 | 5 | 5 | 5 | 2 | 50 |
| Siltech H 1600 | 0 | 6 | 0 | 10 | 25 |
| Siltech H 1700 | 0 | 0 | 0 | 5 | 10 |

These materials are available from Siltech Inc. Norcross Ga.

Fluorine Containing Alcohols

Fluorine containing alcohols are commercially available from a variety of suppliers, most importantly DuPonte Performance Products Division. They conform to the following structure;

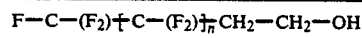

n is ranges from 3 to 17.

| Reactant Example Number | n Value | Molecular Weight | % F |
|---|---|---|---|
| 1 | 3 | 264 | 64.7 |
| 2 | 5 | 364 | 67.8 |
| 3 | 7 | 464 | 69.6 |

-continued

F—C—(F2)—C—(F2)$_n$CH2—CH2—OH n is ranges from 3 to 17.

| Reactant Example Number | n Value | Molecular Weight | % F |
|---|---|---|---|
| 4 | 9 | 564 | 70.7 |
| 5 | 11 | 664 | 71.5 |
| 6 | 13 | 764 | 72.1 |
| 7 | 15 | 864 | 72.5 |
| 8 | 17 | 964 | 72.9 |

Compounds of the Invention

The reaction can be run with varying amounts of fluorine containing alcohol. It should be clear that since only the fluorine containing material contains only one hydroxyl group it will be chain terminating. The other materials, namely the dimethicone copolyol and the diacid each have two functional groups.

Polymers of the following structure will result;

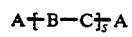

wherein:
A is the fluorine containing portion
B is the diacid
C is the dimethicone copolyol The less amount of "A" used, the higher the "s" value, and the lower the fluorine content. That is because "A" is both a chain stopper and the fluorine source.

| | "A" Concentration High | "A" Concentration Low |
|---|---|---|
| Molecular weight | Low | High |
| Fluorine Content | High | Low |
| "s" value | Low | High |

General Reaction Conditions

The esterification can be run without catalyst; however, when no catalysts used reaction rates are less efficient. Standard esterification catalysts are generally used at concentrations of between 0.05% to 0.50% with a preferred range of 0.1% to 0.3%. Catalysts which are effective include but are not limited to; sulfuric acid, p-toluene sulfonic acid, methane sulfonic acid, tin metal, zinc metal, titanium metal, organo titianates, organo tin compounds, organo zinc compounds, zinc oxide, magnesium oxide, calcium oxide, etc. The most preferred catalyst is stannous oxylate. The reaction is conducted at between 140° and 240° C. under an inert nitrogen blanket. The nitrogen blanket preserves the color. Preferred temperature range is between 180° and 210° C. Water is removed from the reaction which is done using a nitrogen sparge or vacuum.

EXAMPLES

General Procedure

Into a suitable round bottom, three neck flask equipped with a Dean Stark trap, a thermometer and a nitrogen sparge is added the specified number of grams of the diacid, the specified number of grams of dimethicone copolyol, the specified number of grams of fluorine containing alcohol and 0.25% of total weight of the batch of catalyst. The reaction mass is blanketed with nitrogen, and heated to 180° and 200° C. under an inert nitrogen blanket. Once the reaction temperature reaches 120° C. water begins to boil off and is collected in the Dean Stark Trap. Within four to five hours the theoretical water is collected off and the acid value is very low. The product is used without additional purification.

EXAMPLE 9

Into a suitable round bottom, three neck flask equipped with a Dean Stark trap, a thermometer and a nitrogen sparge is added the specified number of 130.0 grams of the Adipic Acid (the diacid), the 5,000.0 grams of Siltech H-1100 (the dimethicone copolyol), 264.0 grams of Reactant Example 1, (the fluorine containing alcohol) and 0.25% of total weight of the batch of catalyst. The reaction mass is blanketed with nitrogen, and heated to 180° and 200° C. under an inert nitrogen blanket. Once the reaction temperature reaches 120° C. water begins to boil off and is collected in the Dean Stark Trap. Within four to five hours the theoretical water is collected off and the acid value is very low. The product is used without additional purification.

EXAMPLE 10–33

Example 9 is repeated only this time substituting the specified number of grams of the specified diacid for the dimer acid and the specified type and number of grams of dimethicone copolyol and the specified type and number of grams of fluorine containing compound as shown below;

Note; In the below table Gms. is grams

| Example | Diacid | "F" Alcohol | Dimethicone Copolyol |
|---|---|---|---|
| 10 | Succinic Acid 102.0 Gms | Reactant Example 2 364.0 Gms. | H-1000 2,329.0 Gms. |
| 11 | Dodecanedioic Acid 230.0 Gms. | Reactant Example 3 464.0 Gms. | H-1100 2,032.0 Gms. |
| 12 | Dimer Acid 286.0 Gms. | Reactant Example 4 564.0 Gms. | H-1200 5,129.0 Gms. |
| 13 | Hydrogenated Dimer Acid 286.0 Gms. | Reactant Example 5 664.0 Gms. | H-1300 347.6 Gms. |
| 14 | Maleic Acid 100.0 Gms. | Reactant Example 6 764.0 Gms. | H-1400 4,407.0 Gms. |
| 15 | Adipic Acid 130.0 Gms. | Reactant Example 7 864.0 Gms. | H-1500 2,783.0 Gms. |
| 16 | Succinic Acid 102.0 Gms. | Reactant Example 8 964.0 Gms. | H-1600 3,550.7 Gms. |
| 17 | Dodecanedioic Acid 230.0 Gms. | Reactant Example 1 264.0 Gms. | H-1700 1,512.4 Gms. |
| 18 | Dimer Acid 286.0 Gms. | Reactant Example 2 364.0 Gms. | H-1000 2,329.0 Gms. |
| 19 | Hydrogenated Dimer Acid 286.0 Gms. | Reactant Example 3 464.0 Gms. | H-1100 2,032.0 Gms. |
| 20 | Maleic Acid 100.0 Gms. | Reactant Example 4 564.0 Gms. | H-1200 2,129.0 Gms. |
| 21 | Adipic Acid 130.0 Gms. | Reactant Example 5 664.0 Gms. | H-1300 347.6 Gms. |
| 22 | Succinic Acid 102.0 Gms. | Reactant Example 6 764.0 Gms. | H-1400 4,407.0 Gms. |
| 23 | Dodecanedioic Acid 230.0 Gms. | Reactant Example 7 432.0 Gms. | H-1500 2,738.0 Gms. |
| 24 | Dimer Acid 286.0 Gms. | Reactant Example 8 964.0 Gms | H-1600 3,550.7 Gms. |
| 26 | Hydrogenated Dimer Acid 286.0 Gms. | Reactant Example 1 133.0 Gms. | H-1700 1,512.4 Gms |
| 27 | Maleic Acid 100.0 Gms. | Reactant Example 2 50.0 Gms. | H-1700 1,512.4 Gms. |
| 28 | Adipic Acid 130.0 Gms. | Reactant Example 3 464.0 Gms. | H-1600 3,550.7 Gms. |
| 29 | Succinic Acid 102.0 Gms. | Reactant Example 4 564.0 Gms. | H-1500 2,738.0 Gms. |
| 30 | Dodecanedioic Acid 230.0 Gms. | Reactant Example 5 664.0 Gms. | H-1400 3,000.0 Gms. |
| 31 | Dimer Acid 286.0 Gms. | Reactant Example 6 764.0 Gms. | H-1300 347.0 Gms. |
| 32 | Hydrogenated Dimer Acid 286.0 Gms. | Reactant Example 7 864.0 Gms. | H-1200 5,000.0 Gms. |
| 33 | Maleic Acid 100.0 Gms. | Reactant Example 8 96.4 Gms. | H-1100 2,032.0 Gms. |

APPLICATIONS EXAMPLES

Compounds of the present invention can be added to water at concentrations ranging from 0.1 to 20% concentration and applied to the hair in creme rinse formulations. Hair treated with these improved conditioner formulations have superior wet comb properties, and have exceptional gloss. Additionally, these formulations having compounds of the present invention present provide good repairative properties to hair that has been treated, permed, or relaxed. The negative effects of the treatment are mitigated.

Additionally, the compounds of the present invention are added to skin lotions at concentrations ranging from 0.1 to 10%. The modified lotions contribute exceptional softness to the skin and provide a non occlusive hydrophobic film on the skin.

What is claimed:

1. A fluorine containing silicone polyester compound which is prepared by the esterification reaction of;

(a) a dimethicone copolyol compound conforming to the following structure;

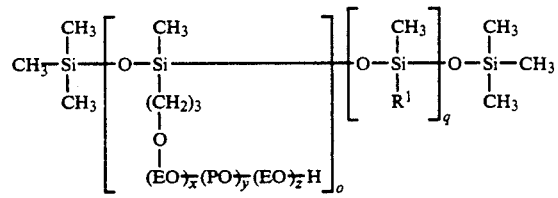

wherein;

$R^1$ is selected from the group consisting of $CH_3$ and phenyl;

EO is $—(CH_2—CH_2—O—)—$

PO is $—(—CH_2—CH(CH_3)—O—)—$ o is an integer ranging from 1 to 20;

q is an integer ranging from 0 to 200;

x, y and z are independently integers each ranging from 0 to 20;

(b) a diacid selected from the group consisting of $HO(O)C—(CH_2)_c—C(O)OH$, $HO(O)C—(CH_2)_d—CH=CH—(CH_2)_e—C(O)OH$ and dimer acid;

c, d and e are independently integers from 1 to 10; and (c) a fluorine containing hydroxy compound conforming to the following structure;

$$F-C-(F_2)+C-(F_2)_{\overline{n}}CH_2-CH_2-OH$$

n is ranges from 3 to 17.

2. A compound of claim 1 wherein the fluorine content in the compound ranges from 5% to 30% by weight.

3. A compound of claim 1 wherein the fluorine content in the compound ranges from 10% to 25% by weight.

4. A compound of claim 1 wherein the diacid is dimer acid.

5. A compound of claim 1 wherein the diacid is dodecanedioic acid.

6. A compound of claim 1 wherein x+y+z is greater than zero.

7. A compound of claim 1 wherein n ranges from 3 to 11.

8. A compound of claim 1 wherein n is 3.

9. A compound of claim 1 wherein n is 5.

10. A compound of claim 1 wherein n is 7.

11. A compound of claim 1 wherein n is 9.

12. A compound of claim 1 wherein n is 11.

13. A compound of claim 1 wherein n is 13.

14. A compound of claim 1 wherein n is 15.

15. A compound of claim 1 wherein n is 17.

* * * * *